United States Patent [19]

Misawa et al.

[11] 4,338,745
[45] Jul. 13, 1982

[54] PROCESS FOR MASS PROPAGATION OF PLANTLETS

[75] Inventors: Masanaru Misawa, Tama; Shinsaku Takayama, Machida; Yoshiki Takashige; Hiroshi Tsumori, both of Hofu, all of Japan

[73] Assignee: Kyowa Hakko Kogyo Kabushiki Kaisha, Tokyo, Japan

[21] Appl. No.: 127,276

[22] Filed: Mar. 5, 1980

[51] Int. Cl.³ .............................................. A01G 1/00
[52] U.S. Cl. ........................................................ 47/58
[58] Field of Search ............................................ 47/58

[56] References Cited

PUBLICATIONS

Tissue Culture of Bulb Scale..., Stimart et al., J. Amer. Soc. Hort. Sci., 103(2): 1978, pp. 182-184.
In Vitro Propagation..., Henny, Hortscience 13(2): Apr. 1978, pp. 150-151.

*Primary Examiner*—Robert E. Bagwill
*Attorney, Agent, or Firm*—Wolder, Gross & Yavner

[57] ABSTRACT

A process for mass propagation of plantlets, which comprises cultivating in vitro a piece of a plant in a medium to obtain an aggregate with stems, leaves, buds, roots, flowers and/or bulbs and cultivating said aggregate in a liquid medium with shaking to obtain plantlets. This process may be applied to a wide variety of plants from Gymnospermae to Angiospermae.

4 Claims, No Drawings

PROCESS FOR MASS PROPAGATION OF PLANTLETS

BACKGROUND OF THE INVENTION

This invention relates to a process for mass propagation of plantlets. More particularly, this invention relates to a process for in vitro production of plantlets. Various processes of this type which are based upon the teaching of Murashige have recently been attempted to mass propagation of various plantlets. Thus, for example, Simmons et al. reported the tissue culture of lilies [Scientia Horiculturae, 5, 161–171 (1976)] and Quorin et al. reported the tissue culture of strawberry [Applied and fundamental aspects of plant cell tissue and organ culture, 130–143 (1977)]. These known processes have various advantages and thus, for example, it is possible to produce a large amount of disease-free and uniform plantlets with a quicker speed in comparison with classical propagation processes and also it is readily possible to establish wide varieties of the desired plants.

SUMMARY OF THE INVENTION

This invention is based upon the discovery that, when a plantlet which has been obtained by cultivating a piece of a plant in a medium and which is to be used for rooting is cultivated in a liquid medium with shaking prior to rooting, it is possible to increase greatly the size of the plantlet and also, the numbers of the plantlet may considerably be increased.

An object of this invention is therefore to provide a process for mass propagation of plantlets, which is capable of saving time-consuming operations which may be needed for example for aseptically dividing an aggregate with stems, leaves, buds, roots and/or bulbs which have been prepared from a meristem of mother plant.

This invention provides a process for mass propagation of plantlets, which comprises cultivating in vitro a piece of a plant in a medium to obtain an aggregate with stems, leaves, flowers, roots, buds and/or bulbs, and cultivating said aggregate in a liquid medium with shaking to obtain plantlets.

Various advantages which may be obtained by the process of this invention are exemplified as follows.

(1) It is possible to save time-consuming operations needed for conventional tissue culture methods, for example, for transplanting the plantlet or the aggregate and excising the same.

(2) It is possible to improve greatly the propagation rate without loss of any advantages which may be obtained by the known methods.

(3) The process of this invention can be carried out by using small numbers of the vessel and also the space for carrying out the process may be saved.

The process of this invention may with advantage be applied to various plants exemplified as follows:

| | |
|---|---|
| Gymnospermae: | |
| Ginkgoaceae | Pinaceae |
| Angiosperma: | |
| Salicaceae | Caryophyllaceae |
| Cruciferae | Vitaceae |
| Violaceae | Primulaceae |
| Apocynaceae | Begoniaceae |
| Gesneriaeae | Compositae |
| Liliiaceae | Amaryllidaceae |
| Iridaceae | |

Thus, it is believed that this may be applied to all higher plants.

PREFERRED EMBODIMENTS

The process of this invention will be explained fully and clearly in the following specification.

A plant tissue such as leaf, stem, bud, flower, root and/or bulb is cut to a piece of the plant tissue (for example, 5×5 mm to 50×50 mm). After sterilizing its surface, for example, by using sodium hypochlorite, ethanol and the like, the piece is put into a solid or liquid medium (e.g. 2 to 10 ml per one piece). By cultivating at a temperature of 10° to 35° C. for about 20 to 70 days, many stems and/or leaves and no or little root differentiate from the piece so that an aggregate comprising mainly the stems and leaves is formed. One or more aggregates thus-formed are put into a vessel containing a sterilized liquid medium and cultivated with shaking. For example, when a 300 ml flask is used, it is preferred to put into the flask 30 to 200 ml of the liquid medium and 1-5 aggregates per 100 ml of the medium and the cultivation is carried out with shaking (for example, 140 to 180 r.p.m.), and when a 3 liter jar fermentor is used, it is preferred to use about 1-2 liter of the medium and 1-5 pieces per 100 ml of the medium and the cultivation is carried out with agitation (250-650 r.p.m.) and aeration (0.5 to 3 liter/minute). In both cases, the cultivation is carried out at a temperature of 10° to 35° C. When the cultivation is continued for example for more than 15 to 40 days, it is possible to obtain a grown plantlet which may be used as a seedling without further treatment. However, when two or more plantlets are cultivated in one vessel, in some cases, the roots of these plantlets are entangled with each others so that any post-treatment becomes more or less difficult. Thus, in such cases, it is possible if desired to separate the plantlets into individuals and transplant them into other media (for example agar media) in order to carry out a further cultivation which may also be carried out for example at a temperature of 10° to 35° C. for 10 to 30 days under static conditions. When it is desired to elongate the culture time or store the seedling, a lower temperature (for example 0°-10° C.) is preferred for this purpose.

The choice of meristem on the mother plant does not give any deleterious influence upon this process of this invention, although young plants are preferable. It is preferred to use any and all media which may be used for usual tissue culture processes and which include suitable carbon sources (e.g. sugars), inorganic nitrogen sources, nitrogen-containing organic sources, inorganic salts, metalic ions, cytokanins such as kinetin, auxines such as 2,4-dichlorophenoxy acetic acid, naphthaleneacetic acid (hereinafter referred to as NAA) or indoleacetic acid, and if desired, adequate amounts of growth-promoting hormones such as gibberellin, abscisic acid and the like. When kinetin or cytokinin is used, each amount is preferably 1-10 mg/l or 0.3-10 mg/l. Of course, it is also possible to use various media of the known types conventionally used for tissue culture techniques such as for example Murashige-Skoog's medium, Linsmayer-Skoog's medium, White's medium, Knop's medium and the like as well as the modified media thereof. The pH of the media used for the process of this invention is usually from 3.5 to 8.5.

The composition of the medium used for the liquid culture with skaking according to this invention may be the same as or different from those of other media used before or after the liquid culture with shaking. Thus, it is advantageous to use the media having the same composition with or without the solidifying agent such as for example agar for different purposes.

For carrying out the cultivation of this invention, the illumination is usually not needed. However, in some cases, it may be possible to obtain better results by using an illumination (for example, 200 to 10,000 lux).

When the process of this invention is applied to any plant having bulb such as the plants belonging to Liliflorae (e.g. Liliaceae, Amaryllidaceae and Iridaceae), the treatments may be modified as follows.

(A) Any tissue and/or organ of the plant may be used as the material to be cultivated in a medium (preferably solid medium such as agar medium), although it is advantageous for practical purpose to use the bulb as the material. In this case, a bulb (preferably combined with the disc) is cut to small pieces (5×5 mm to 50×50 mm). For example, one or several pieces are put into a medium, of which volume may be from 2 to 10 ml per one piece, and are cultivated at a temperature of from 10° to 35° C. for 20 to 60 days. By this cultivation, one to several bulblets differentiate from each piece and also no or little root may differentiates.

(B) Each scale is removed from the thus-obtained bulblet and is put on a medium (preferably solid medium) containing adequate substances and cultivated, so that an aggregate with mainly new scales which have differentiated from the transplanted scale. In this step, the cultivation is carried out at a temperature of from 10° to 35° C. for 20 to 60 days under static conditions.

(C) The thus-obtained aggregate with mainly the scales is put into a liquid medium and cultivated with shaking so that the scales rapidly and greatly enlarge or grow. After that, the scales are separated from the aggregate into individuals.

As the liquid medium, it is preferred to use a medium having the same composition as that of the medium used in (A) except agar. For example, when a 300 ml flask containing 30 to 200 ml of the medium is used, one to five aggregates per 100 ml of the medium are put into the flask and cultivated at a temperature of from 10° to 35° C. with shaking of 140 to 250 r.p.m. and when a 3 liter jar fermentor containing a liquid medium (1 to 2 liter) is used, one to five aggregates per 2 liter of the medium are put into the jar and cultivated at the same temperature with shaking (250 to 650 r.p.m.) and aeration (0.5 to 3 liter/min.).

When the cultivation is carried out for example for more than about 20 to 40 days, the bulblets thus-obtained are sufficient to use as the seedlings without any post-treatment. However, in order to save time and operations which may be needed therefor, it is advantageous to discontinue the further cultivation and to transfer the formed bulblets to the next step.

(D) Each bulblet is taken out from the vessel and the scales are separated into individuals, each of which is further cultivated in a liquid or solid medium having the same composition as used in the foregoing treatment under static conditions or in a similar liquid medium with shaking. In this manner, new bulblets may be formed and also it is possible if desired to obtain such a bulblet that may be used as the seedling without any further treatment.

In the case of static culture, this may be carried out at a temperature of from 10° to 30° C. for 30 to 100 days, and in the case of shaking culture, this for example may be carried out at a temperature of from 10° to 35° C. for 20 to 50 days with shaking of from 140 to 250 r.p.m. If desired, the cultivation may be carried out at a lower temperature such as e.g. from 0° to 10° C. in order to elongate the cultural period.

In this manner, it may be roughly estimated that a middle-sized bulb of lily may produce the plantlets at a propagation rate of $125 \times 10^6$ (in the case of Lilium speciosum) or $324 \times 10^9$ (in the case of Lilium auratum) in one year.

The following non-limiting examples illustrate the invention.

EXAMPLE 1

Begonia:

Leaves of a Rieger begonia (*Begonia xelatior*) were sterilized with 30% Na-hypochlorite and after that with 70% ethanol, washed with sterilized water an cut to small pieces (approximately 5×5 mm of each piece). Fifteen pieces were put on an agar medium whose composition was indicated in Table 1, in a Petri dish (diameter: 9 cm, depth 2 cm). They were cultivated at 25° C. for 25 days under 2,500 lux.

TABLE 1

| | | | |
|---|---|---|---|
| $NH_4NO_3$ | 1650 mg | Vitamin B1 | 0.40 mg |
| $KNO_3$ | 1900 mg | Inositol | 100 mg |
| $CaCl_2 \cdot 2H_2O$ | 440 mg | Hydrochloride | 0.50 mg |
| $MgCl_2 \cdot 7H_2O$ | 370 mg | Nicotinic acid | 0.50 mg |
| $KH_2PO_4$ | 170 mg | Glycine | 2.00 mg |
| Disodium EDTA—$2H_2O$ | 37.3 mg | Sucrose | 30.0 g |
| $FeSO_4 \cdot 7H_2O$ | 27.8 mg | Agar | 8.0 g |
| $H_3BO_3$ | 6.2 mg | Naphthalene acetate (NAA) | 1.00 mg |
| $MnSO_4 \cdot 4H_2O$ | 22.3 mg | Benzyladenine (BA) | 0.3 mg |
| $ZnSO_4 \cdot 7H_2O$ | 8.6 mg | | |
| KI | 0.83 mg | | |
| $Na_2MoO_4 \cdot 2H_2O$ | 0.25 mg | | |
| $CuSO_4$ | 0.025 mg | | |
| $CoCl_2$ | 0.025 mg | | |

(These components were dissolved in deionized water to make up one liter, adjusted to pH of 6.3 and then sterilized.)

Each piece of the leaf enlarged and as a result, about 400 stems and leaves were differentiated from an aggregate formed from the piece. This aggregate was divided into 4 small aggregates and each of them was transferred to 300 ml of liquid medium whose composition was the same as described in Table 1 except omission of agar. After cultivation on a rotary shaker (180 r.p.m., amplitude 5 cm) at 25° C. for 14 days under 300 lux, approximately 500 stems (length 1–3 cm) and/or leaves were developed from the aggregate but roots were scarcely observed. The aggregate with the stems and-/or the leaves thus obtained was aseptically taken out from the beaker and these differentiated organs were individually separated from the aggregate. Fifteen individuals were transferred to the agar medium as described in Table 1 but without benzyladenine (BA) in a Petri dish (diameter 9 cm, depth 2 cm). During 10 days cultivation of the individuals at 25° C. under 500 lux, the roots were differentiated from them. They grew rapidly to plantlets which had the stems, the leaves and the roots.

In Example 1, approximately 2,000 plantlets were obtained from a 5×5 mm sized piece of the leaves after 50 days. They were transferred to the soil and cultivated in an usual way. These plants thus obtained came into bloom as well as those propagated by the classical method.

EXAMPLE 2

Begonia (Rieger):

The same procedures as described in Example 1 were repeated except using a 3 liter glass jar fermentor as a vessel containing 2 l of the liquid medium for the cultivation. The aggregates were incubated in the fermentor for 10 days and at 2 l/minute of the aeration rate. About 8,000 plantlets were produced after about 50 days cultivation from 4 of 5×5 mm sized pieces of the leaf.

EXAMPLE 3

Begonia:

The same procedures as described in Example 1 were repeated with a piece of the stem cut from *Begonia semperiflorens* instead. However, in this example, 0.1 mg/l 2,4-dichlorophenoxy acetic acid (2,4-D) and 0.1 mg/l kinetin were used instead of naphthalene acetic acid (NAA) and BA as growth regulators. The cultural period of the plant pieces on the agar medium at the first stage was shortened to 20 days. Approximately 250 of plantlets were produced from a 1 cm of piece of the stem.

EXAMPLE 4

Begonia:

The same procedures as described in Example 1 were repeated with a 5×5 mm sized piece of the leaf of *Begonia tuberhybrida* instead. Approximately 1,000 of plantlets were produced after about 50 days cultivation.

EXAMPLE 5

Goldband lily (*Lilium auratum*):

The surface of a bulb of *L. auratum* was sterilized with 30% Na-hypochlorite and after that with 70% ethanol and then cut to small cubes (each size was about 5 mm cube). Each cube was put on 10 ml agar medium in a test tube. The composition of the medium was the same as that described in Table 1 but contained 0.1 mg/l NAA as an only growth regulator. After 45 days cultivation at 25° C. under 2,500 lux, about 1 to 5 bulblets were differentiated from each cube. The bulbscales in the bulblets thus obtained were aseptically separated and transferred to 50 ml of the agar medium in a Petri dish (diameter 9 cm, depth 2 cm). Ten mg of kinetin per liter was added to the above-described medium. After 50 days cultivation at 25° C. under 2,500 lux, each bulbscale grew to an aggregate with 250 of 0.1 to 1.0 cm bulbscale. These new differentiated bulbscales in the aggregate were, however, too small to use as materials for further treatment. Therefore, one of the aggregates was transferred to 100 ml of the liquid medium in a 300 ml conical beaker and cultivated in suspension at 25° C. on a rotary shaker operated at 180 r.p.m. and 5 cm of amplitude under 300 lux. The medium used was the same as described in Table 1 except omission of agar and addition of 90 g/l sucrose. After cultivation for 25 days, the bulbscales grew up to 0.5-4.0 cm in length. The aggregate having the bulbscales was aseptically taken out from the beaker and the scales were individually separated from the aggregate. To the agar medium in a Petri dish (diameter 9 cm and depth 2 cm), 15 of the scale were transferred and cultivated statically for 60 days at 25° C. The medium used was the same as described in Table 1 with the exception of 90 g/l sucrose. During cultivation, the scales enlarged, differentiated bulblets and roots and finally formed bulbs. In this manner, numerous plantlets of lily were produced.

According to this example, approximately 10,000 of new bulb scales were obtained from a scale in a middle sized parent bulb after 120 days. And approximately 25,000 of plantlets were produced by further cultivation for 60 days of these bulbscales on the agar medium. They were transferred to the soil and cultivated in an usual way. These plant thus obtained came into bloom as well as those propagated by the classical method.

EXAMPLE 6

Goldband lily (*Lilium auratum*):

Fifteen scales obtained in the same manner as in Example 5 were transferred to 100 ml of the liquid medium having the same composition as in Table 1 of Example 1 except omission of agar and addition of 0.1 mg/l NAA in a 300 ml Erlenmeyer flask and cultivated at 25° C. for 30 days on a rotary shaker operated at 180 r.p.m. and 5 cm of amplitude to obtain almost the same numbers of plantlets as that of plantlets in Example 5.

EXAMPLE 7

Goldband lily (*Lilium auratum*):

The same procedures as described in Example 5 were repeated except that as liquid cultivation, the cultivation was carried out for 25 days at 2 l/min. of the aeration rate using a 3 l glass jar fermentor containing 2 l of medium. Approximately 10,000 of new bulbscales were obtained from a scale in a middle sized parent bulb after 120 days of cultivation.

The thus obtained newbulbs were transferred to a 3 l glass jar fermentor having 2 l of the liquid medium instead of Erlenmeyer flask of Example 6 and cultivated at 25° C. for 50 days at 1 l/min. of aeration rate to obtain about 25,000 plantlets.

EXAMPLE 8

*Lilium speciosum:*

The same procedures as described in Example 5 were repeated except that the scales of *Lilium speciosum* were used instead of that of *Lilium auratum*, the agar medium having the same composition as in Table 1 except addition of 1 mg of benzyladenine and the same liquid cultivation as described in Example 7 was repeated.

Approximately, 100,000 new bulbscales were obtained from a scale in a middle sized parent bulb after 120 days of cultivation. The thus obtained newbulbs were transferred to a 20 l glass jar fermentor having 15 l of the liquid medium instead of 5 l jar fermentor of Example 7 and cultivated for 50 days at 7 l/min. of aeration rate to obtain about 250,000 plantlets.

EXAMPLE 9

*Lilium longiflorum:*

The same cultivation using agar medium as described in Example 5 was repeated except that *Lilium longiflorum* was used instead of *Lilium auratum*.

The piece of the growing part was cut from the thus obtained bulb under microscope and transferred to the same agar medium as described in Example 5.

Cultivation was carried out at 25° C. for 60 days under 2,500 lux to obtain new virus-free bulbs.

The scale of the thus obtained bulb was cultivated on agar medium in the same manner as described in Example 5. Approximately, 20,000 of plantlets were obtained from a scale of the middle size of bulb in a period of about 230 days.

EXAMPLE 10

Japanese red pine (*Pinus densiflora*):

The terminal 3 cm of a shoot was cut off from a seedling of Japanese red pine of 5 years old, growing in a seedling field. After sterilizing the surface by dipping into 2% Na-hypochlorite solution for 25 minutes, the sample was washed with sterilized water.

Then the sample was transferred to 10 ml of the agar medium prepared by adding 1 mg/l NAA, 30 mg/l kinetin, 10 g/l sucrose and 8 g/l agar to Murashige-Skoop medium in a test tube. After 60 days of cultivation at 25° C. under 2,500 lux, an aggregate having many buds on its surface was obtained. The aggregate was transferred to a 300 ml conical beaker containing 50 ml of a liquid medium having the same composition as described-above except omission of agar and addition of 2 mg/l kinetin. After 80 days of cultivation at 25° C. on a rotary shaker operated at 180 r.p.m. and 5 cm of amplitude under 300 lux, about 80 plantlets having a length of 0.5-3 cm were obtained per a flask.

EXAMPLE 11

Ginkgo (*Ginkgo biloba*):

At an early stage of growing, a bud having a length of about 2 mm was aseptically cut off from a shoot of a 50 years old Ginkgo growing in wild. The sample was transferred to a liquid medium prepared by adding 0.5 mg/l NAA, 1 mg/l kinetin and 30 g/l sucrose to Murashige-Skoog medium. Cultivation was carried out at 25° C. for 30 days under 2,500 lux to obtain a plantlet having a length of about 2 cm. Then the plantlet was transferred to the agar medium (pH: 6.3) having the same composition as described above except addition of 20 mmg/l kinetin and 8 g/l of agar.

After 60 days of cultivation, 5-30 auxiliary buds were developed from the plantlet. The buds were transferred to 50 ml of the same liquid medium as described above except addition of 1 mg/l kinetin in a 300 ml conical beaker. After 50 days of cultivation under the similar conditions to those described in Example 10, 10-20 plantlets having a length of about 3 cm were obtained per flask.

EXAMPLE 12

Carnation (*Dianthus caryophyllus*) 1:

A bud (length: 0.2 mm) of Carnation was aseptically cut off and transferred to a test tube containing 10 ml of an agar medium prepared by adding 0.1 mg/l NAA, 0.01 mg/l kinetin, 30 g/l sucrose and 6 g/l agar to Murashige-Skoog medium. After 3 weeks of cultivation at 25° C. under 2,500 lux, the sample grew up to plantlet having a length of 0.5-2 cm. Then, the plantlet was transferred to a 300 ml conical beaker containing 50 ml of a liquid medium prepared by diluting Murashige-Skoog medium 3 times with water and adding 0.1 mg/l NAA, 0.5 mg/l kinetin and 30 g/l sucrose. After 30 days of cultivation at 25° C. under lighting with shaking of 180 r.p.m., approximately 20 auxiliary buds having a length of 0.5-2 cm were developed from each plantlet. These buds were easily separated from the mother plantlet. The bud was subjected to liquid cultivation two times in the similar manner to that described above to obtain 25,000 plantlets from the starting bud in a period of about 110 days.

The thus-obtained plantlet was transplanted to the medium for developing root prepared by adding 0.5 mg/l NAA, 10 g/l sucrose and 8 g/l agar to Murashige-Skoog medium and was incubated to obtain a seedling. The seedling was transplanted onto the soil and then normal flowering was observed.

EXAMPLE 13

Carnation (*Dianthus caryophyllus*):

The same procedures as described in Example 12 were repeated except that 250 plantlets derived from the buds were cultivated in a 10 l jar fermenter containing 7 l liquid medium at 25° C. for 30 days with aeration of 2.5 V.V.M. under 500 lux to obtain 2,500 plantlets.

EXAMPLE 14

African violet (*Saintpaulia ionantha*):

A sterilized leaf of *Saintpaulia ionantha* was cut into pieces (approximately 5×5 mm) and transferred into a test tube containing 10 ml of an agar medium (pH: 6.3) prepared by adding 1 mg/l NAA, 0.3 mg/l benzyladenine, 10 g/l sucrose and 8 g/l agar to Murashige-Skoog medium.

After 25 days of cultivation at 25° C. under 2,500 lux, the piece enlarged and an aggregate having about 150 stems and leaves was obtained. The aggregate was transferred into a 300 ml conical beaker containing 100 ml of a liquid medium having the same composition as described above except omission of agar.

After 20 days of cultivation at 25° C. under 300 lux on a rotary shaker operated at 180 r.p.m. and 5 cm of amplitude, an aggregate having about 200 stems (length: about 1-3 cm) leaves (diameter: about 0.5-3 cm) was obtained. The aggregate was aseptically taken out from the beaker and these differentiated organs were individually separated. Then the organs were transplanted to the soil and cultivated in a usual way to obtain 10,000 seedlings from a mother leaf in a period of 50 days.

EXAMPLE 15

Gloxinia (*Sinningia speciosa*):

After sterilizing the surface of a leaf of Gloxinia, the leaf was cut into a piece (5×5 mm) and was transferred into a test tube containing 10 ml of an agar medium (pH: 6.3) prepared by adding 0.1 mg/l NAA, 2 mg/l kinetin, 1% sucrose and 8 g/l agar to Murashige-Skoog medium. After 30 days of cultivation at 25° C. under 2,500 lux, about 60 buds were developed on the surface of the leaf. Then, the aggregate with the buds was transferred to a 300 ml conical beaker containing 50 ml of a liquid medium (pH: 6.3) having the same composition as described above except omission of agar. Thus, about 60 plantlets having a length of 1-4 cm were obtained. For developing roots, the plantlet was transferred onto a Petri dish containing a medium (pH: 6.3) having the same composition as described above except addition of 1 mg NAA and omission of kinetin and incubated for 15 days to develop roots. In this manner, about 4,000 plantlets having roots were obtained from a piece of leaf in a period of 80 days.

EXAMPLE 16

Madagascar periwinkle (*Catharanthus roseus*):

A stem of *Catharanthus roseus* was used as a sample, from which the leaves had been removed at the base of each petiole. The sample was sterlized with 2% Na-hypochlorite solution and cut into pieces at the nodes. Then each piece was transferred into a test tube containing 10 ml of an agar medium prepared by adding 1 mg/l benzyladenine, 30 g/l sucrose and 8 g/l agar to Murashige-Skoog medium. After 30 days of cultivation at 25° C. under 2,500 lux, an aggregate having about 50 auxiliary buds was obtained. The aggregate was transferred into a 300 ml conical beaker containing 50 ml of a liquid medium (pH: 6.3) having the same composition as described above except omission of agar. After 30 days of cultivation at 25° C. on a rotary shaker (180 r.p.m.), plantlets (length: 1–4 cm) having auxiliary buds were obtained. The plantlets was aseptically taken out from the beaker and divided into each plantlet. For developing root, the each plantlet was transferred onto an agar medium (pH: 6.3) having the same composition as described above except omission of benzyladenine and addition of 1 mg/l NAA. After 15 days of cultivation at 25° C. under 5,000 lux, about 50 plantlets were obtained per a flask.

EXAMPLE 17

Barberton daisy (*Gerbera jamesonii*):

A bud (length: 6 mm) of the stem of *Gerbera jamesonii* was aseptically taken out and sterilized with 2% Na-hypochlorite solution. Then, the sample was transferred into a test tube containing 10 ml of an agar medium (pH: 6.3) prepared by adding 0.5 mg/l NAA, 10 mg/l kinetin, 45 g/l sucrose and 8 g/l agar to Murashige-Skoog medium. After 4 weeks of cultivation at 25° C., an aggregate having 8 auxiliary buds was obtained. The aggregate was transferred onto a liquid medium (pH: 6.3) having the same composition as described above except omission of agar. After 30 days of cultivation at 25° C. on a rotary shaker (180 r.p.m.), about 40 plantlets (length: 0.5–5 cm) having auxiliary buds were obtained. The plantlets were aseptically divided into segments. The segments were transferred to the liquid medium having the same composition as described above. Then cultivation was repeatedly carried out. As a result, about 300 plantlets were obtained. The plantlets were aseptically divided into each plantlet. Then, for developing root each plantlet was transferred onto 10 ml of an agar medium (pH: 6.3) prepared by adding 10 mg/l NAA, 30 g/l sucrose and 8 g/l agar to Murashige-Skoog medium in a Petri dish (diameter 9 cm, depth 2 cm). After 2 weeks of cultivation at 25° C. under 5,000 lux, plantlets were obtained.

EXAMPLE 18

*Primula malacoides:*

A bud (about 2 mm) of *Primula malacoides* was aseptically collected and transferred into a test tube containing 10 ml of an agar medium (pH: 6.3) prepared by adding 0.1 mg/l NAA, 1 mg/l kinetin, 30 g/l sucrose and 8 g/l agar to Murashige-Skoog medium. After 40 days of cultivation at 25° C., plantlets having a length of about 2 cm were obtained. Then 20 plantlets were transferred onto an other 50 ml of agar medium having the same composition as described above except that the amount of kinetin was 3 mg/l in a Petri dish (diameter 9 cm, depth 2 cm). After about 40 days of cultivation at 25° C., plantlets having about 5 auxiliary buds were obtained. Five plantlets were transferred into a 300 ml conical beaker containing 50 ml of a liquid medium (pH: 6.3) prepared by adding 0.1 mg/l NAA, 1 mg/l kinetin and 30 g/l sucrose to Murashige-Skoog medium. After 30 days of cultivation at 25° C. on a rotary shaker (180 r.p.m.), aggregates (length: 1–4 cm) havng auxiliary buds were obtained. The aggregates were aseptically divided into segments. Then, for developing root 15 segments were transferred onto a Petri dish (diameter 9 cm, depth 2 cm) containing 50 ml of an agar medium (pH: 6.3) prepared by adding 1 mg/l NAA, 30 g/l sucrose and 8 g/l agar to Murashige-Skoog medium. After 15 days of cultivation at 25° C. under 5,000 lux, plantlets were obtained.

EXAMPLE 19

*Chrysanthemum morifolium:*

A bud (length: 0.2 mm) of *Chrysanthemum morifolium* was aseptically collected and transferred into a test tube containing 10 ml of a liquid medium (pH: 6.3) prepared by adding 0.02 mg/l NAA, 2 mg/l kinetin and 30 g/l sucrose to Murashige-Skoog medium. After 3 weeks of cultivation at 25° C. under 2,500 lux, a plantlet having a length of about 3 cm was obtained. The plantlet was transferred into a 300 ml conical beaker containing 50 ml of a liquid medium having the same composition as described above. After 4 weeks of cultivation at 25° C. on a rotary shaker (180 r.p.m.) under 300 lux, an aggregate with about 60 auxiliary buds were obtained. The aggregate was divided into plantlets. The plantlets were transferred onto new media having the same composition as described above. Cultivation was carried out under the same conditions as described above and about 4,000 plantlets were obtained. Then, for developing root 20 of the plantlets were transferred onto a Petri dish (diameter 9 cm, depth 6 cm) containing 50 ml of an agar medium (pH: 6.3) prepared by adding 0.02 mg/l NAA, 30 g/l sucrose and 8 g/l agar to Murashige-Skoog medium. After 15 days of cultivation at 25° C. under 2,500 lux, about 4,000 plantlets were obtained.

EXAMPLE 20

Girasole (*Helianthus tuberosus*):

At an early stage of the budding of Girasole, a short apex (2 cm) was sliced off from the tuber. The apex was sterilized with 2% Na-hypochlorite solution and washed with water. Then, the apex was transferred into a test tube containing 10 ml of an agar medium (pH: 6.3) prepared by adding 0.1 mg/l NAA, 3 mg/l kinetin, 30 g/l sucrose and 8 g/l agar to Murashige-Skoog medium. After 40 days of cultivation at 25° C. under 2,500 lux, a plantlet (height: 5 cm) having about 30 auxiliary buds (length: 0.1–2 cm) was obtained. The plantlet was transferred into a 300 ml conical beaker containing 50 ml of a liquid medium (pH: 6.3). After about 30 days of cultivation at 25° C. on a rotary shaker (180 r.p.m.) under 300 lux, an aggregate was obtained. The aggregate was aseptically divided into segments. Then, each segment was put into an another agar medium. After 40 days of cultivation at 25° C. under 2,500 lux, a plantlet having grown auxiliary buds was obtained. The plantlet was aseptically divided into segments. Then for developing root each segment was transferred onto a Petri dish (diameter 9 cm, depth 6 cm) containing 100 ml of an agar medium (pH: 6.3) prepared by adding 3 mg/l NAA, 30 g/l sucrose and 8 g/l agar to Murashige-Skoog medium. After 20 days of cultivation at 25° C. under 5,000 lux, about 800 plantlets were obtained.

EXAMPLE 21

*Agrostemma githago:*

A stem of *Agrostemma githago* was sterilized with 3% Na-hypochlorite solution, washed with sterilized water and cut into pieces at every node. The pieces were transferred into a test tube (5 pieces per tube) containing 10 ml of an agar medium (pH: 6.3) prepared by adding 0.1 mg/l NAA, 0.1 mg/l kinetin, 30 g/l sucrose and 8 g/l agar to Murashige-Skoog medium. After 30 days of cultivation at 25° C. under 300 lux, plantlets having auxiliary buds were obtained. Then 5 plantlets were transferred into a 300 ml conical beaker containing 50 ml of a liquid medium (pH: 6.3) having the same composition as described above except omission of agar. After 30 days of cultivation at 25° C. on a rotary shaker (180 r.p.m.) under 300 lux, about 40 plantlets were obtained. Then each plantlet was divided into 5 pieces and each of 5 pieces was cultivated in a liquid medium for 30 days under the same conditions as described above. In this manner, about 700 plantlets having a length of 1-4 cm were obtained. Then for developing root each of 15 plantlets was transferred onto a Petri dish (diameter 9 cm, depth 2 cm) containing 40 ml of an agar medium (pH: 6.3) prepared by adding 0.5 mg/l NAA, 30 g/l sucrose and 8 g/l agar to Murashige-Skoog medium. After 15 days of cultivation at 25° C. under 5,000 lux, plantlets were obtained.

EXAMPLE 22

Fox-grape (*Vitis labrusca* L.):

An elongating branch of Fox-grape was collected, washed with 1% Na-hypochlorite solution and washed with sterilized water. Each piece (length: about 1 cm) with auxiliary buds was collected and transferred into a test tube containing 10 ml of an agar medium (pH: 6.3) prepared by adding 0.1 mg/l NAA, 10 mg/l kinetin, 30 g/l sucrose and 8 g/l agar to Murashige-Skoog medium. After about 30 days of cultivation at 25° C., buds having many branchings were obtained. Then each of the buds was transferred into 300 ml conical beaker containing 50 ml of a liquid medium (pH: 6.3) having the same composition as described above except omission of agar. After 30 days of cultivation at 25° C. under 300 lux, plantlets (lengths: 1-3 cm) having auxiliary buds were obtained. The plantlets were aseptically divided into each plantlet. Then each plantlet was further cultivated by using the above-mentioned agar and liquid media, 15 plantlets were obtained. Then 15 plantlets were transferred into a Petri dish (diameter 9 cm, depth 2 cm) containing 100 ml of an agar medium (pH: 6.3) prepared by adding 2 mg/l NAA, 0.5 mg/l kinetin, 30 g/l sucrose and 8 g/l agar to Murashige-Skoog medium. After 20 days of cultivation at 25° C. under 5,000 lux, about 600 plantlets were obtained.

EXAMPLE 23

Amaryllis (*Hippeastrum hybridum*)

A bulb of Amaryllis was sterilized with 70% ethanol solution, washed with sterilized water and sliced into some pieces comprising a part of the disc. Each piece was put into a test tube containing 10 ml of an agar medium (pH: 6.3) prepared by adding 30 g/l sucrose and 8 g/l agar to Murashige-Skoog medium. After 60 days of cultivation at 25° C., each piece having 2-5 new bulblets (diameter: about 5 cm) was obtained. The each piece was divided into 4 equal pieces in the longitudinal direction. Then each piece was transferred onto 10 ml of an agar medium (pH: 6.3) prepared by adding 10 mg/l kinetin, 0.1 mg/l NAA, 30 g/l sucrose and 8 g/l agar to Murashige-Skoog medium. After 60 days of cultivation at 25° C., aggregates having about 30 buds were obtained. Then, 5 aggregates were put into a 300 ml conical beaker containing 100 ml of a liquid medium (pH: 6.3) prepared by adding 60 g/l sucrose to Murashige-Skoog medium. After 30 days of cultivation at 25° C. on a rotary shaker (180 r.p.m.), about 100 bulbs per beaker were obtained.

EXAMPLE 24-33

Table 2 shows that various plantlets were rapidly, obtained when various plants were treated in the same procedures as mentioned in Examples described above.

TABLE 2

| No. | Plant | Material | Propagation ratio/year* | Applied Example |
|---|---|---|---|---|
| 24 | Daffodil (*Narcissus tazetta* L. var. *chinensis*) | One bulb | $10^5$ | 23 |
| 25 | *Gladiolus gandavensis* | One bulb | $2.5 \times 10^5$ | 23 |
| 26 | *Freesia refracta* | One bulb | $2 \times 10^4$ | 23 |
| 27 | *Iris hollandica* | One whole plant | $4 \times 10^3$ | 23 |
| 28 | *Tulipa gesneriana* | One bulb | $3 \times 10^4$ | 23 |
| 29 | *Polygonatum falcatum* | One whole plant | $4 \times 10^4$ | 23 |
| 30 | *Ophiopogon japonicus* | One whole plant | $3 \times 10^3$ | 11 |
| 31 | *Salix koriyanagi* | One bud | $1.5 \times 10^5$ | 22 |
| 32 | *Wasabia japonica* | One bud | $10^4$ | 20 |
| 33 | *Viola eizaensis* | One bud | $10^6$ | 18 |

What is claimed is:

1. A process for mass propagation of a morphologically normal bulb of a plant selected from the group consisting of Liliaceae, Amaryllidaceae and Iridaceae, which process comprises cultivating a piece of morphologically normal bulb of the said plant in a first medium selected from an agar medium and a liquid medium under sterilized conditions to give at least two bulblets differentiated from the said bulb piece, removing the bulbscales from the said bulblets, cultivating said scale in a second medium selected from an agar medium and a liquid medium with shaking under sterilized conditions to give at least one aggregate per one scale, removing new bulbscales from the said aggregate, cultivating the said new bulbscales in a liquid medium under sterilized conditions to obtain a new bulblet per one new scale, and cultivating the said new bulbet in a fourth medium selected from an agar medium and a liquid medium under sterilized conditions to obtain a morphologically normal bulb.

2. A process according to claim 1, in which the plant is selected from the group consisting of *Lilium auratum, Lilium speciosum, Lilium longiflorum, Tulipa gesneriana, Polygonatum falcatum, Ophiopogon japonicus, Hippeastrum hybridum, Narcissus tazetta, Gladiolus gandavensis, Freesia refracta* and *Iris hollandica*.

3. A process according to claim 1 in which the cultivation is effected at a temperature of 10°-35° C.

4. The process of claim 1 in which the plant is *Lilium longiflorum*.

* * * * *